United States Patent
Mayenberger

Patent Number: 5,853,412
Date of Patent: Dec. 29, 1998

[54] BIPOLAR SURGICAL GRASPING INSTRUMENT

[75] Inventor: Rupert Mayenberger, Rielasingen, Germany

[73] Assignee: Aesculap AG & Co. KG, Tuttlingen, Germany

[21] Appl. No.: 810,763

[22] Filed: Mar. 5, 1997

[30] Foreign Application Priority Data

Mar. 6, 1996 [DE] Germany .................. 196 08 716.3

[51] Int. Cl.⁶ .................................................. A61B 17/39
[52] U.S. Cl. .............................. 606/51; 606/45; 606/207
[58] Field of Search ........................... 606/41, 45, 46, 606/1, 52, 205, 208

[56] References Cited

U.S. PATENT DOCUMENTS

| | | | |
|---|---|---|---|
| 5,312,434 | 5/1994 | Crainich | 606/207 |
| 5,331,971 | 7/1994 | Bales et al. | 606/205 |
| 5,352,222 | 10/1994 | Rydell . | |
| 5,356,408 | 10/1994 | Rydell | 606/48 |
| 5,391,166 | 2/1995 | Eggers . | |
| 5,462,546 | 10/1995 | Rydell | 606/51 |
| 5,540,685 | 7/1996 | Parins et al. | 606/51 |
| 5,607,450 | 3/1997 | Zvenyatsky et al. | 606/206 |
| 5,697,949 | 12/1997 | Giurtino et al. | 606/206 |

FOREIGN PATENT DOCUMENTS 39 17 328 11/1990 Germany .
43 12 284 11/1993 Germany .

*Primary Examiner*—Michael Peffley
*Attorney, Agent, or Firm*—Barry R. Lipsitz; Ralph F. Hoppin

[57] ABSTRACT

A bipolar surgical grasping instrument with two grasping arms that are electrically insulated from one another. The two arms are pivotally mounted at the end of a tubular shank, and are coaxially pivotable in opposite directions by toggle lever elements that are activated by a push-and-pull rod displaceable in the tubular shank. The push-and-pull rod and the toggle lever elements of the two arms consist of electrically conducting material and are electrically conductively connected to one another. The first arm is electrically conductively connected to it associated toggle lever elements. The second arm is connected to its associated toggle lever elements via an insulating part, and the second arm is electrically conductively connected via a pivot bearing to the tubular shank. The first arm is rotatably mounted on the tubular shank and electrically insulated from the second arm and from the tubular shank.

20 Claims, 4 Drawing Sheets

BIPOLAR SURGICAL GRASPING INSTRUMENT

BACKGROUND OF THE INVENTION

The invention relates to a bipolar surgical grasping instrument comprising two arms which are pivotably mounted at the end of a tubular shank and are coaxially pivotable by means of toggle lever elements in opposite directions by a push-and-pull rod displaceable in the tubular shank.

Use of tubular shank instruments in which arms of a tool pivotable relative to each other, for example, legs of forceps or legs of scissors, can be separately connected to the different poles of a high-frequency voltage source so that high-frequency currents can flow between the arms of this tool, which are electrically isolated from each other, in order to coagulate and cut tissue lying therebetween, is desirable, in particular, in endoscopic operations.

Owing to the small dimensions of such instruments, it is extremely difficult to achieve reliable electric insulation of the two arms, on the one hand, and a simple construction, on the other hand.

It is, for example, known from U.S. Pat. No. 5,391,166 to pivotably mount two arms in a tubular shank of a grasping instrument. Complicated individual parts are necessary for separating these arms electrically from each other. In particular, intermediate insulating members, insulating pivot pins and insulative coatings on the arms are required, and these insulative coatings may only be partially provided. In the known construction, it is also necessary for two electric leads to be arranged inside the tubular shank, and these have to be connected to a plug-in connection with a special adapter. As a whole, this results in a rather complicated construction, with which it is also not possible to do with a single push-and-pull rod in the conventional way, as two separate electric leads are necessary in the interior of the tubular shank.

This also applies to another construction described in U.S. Pat. No. 5,352,222. Here, too, two separate conductive rods are necessary. Furthermore, both arms of the tool have to be assembled in a complicated, sandwich-like manner as the opposed blades of the scissors-like instrument are to be separated from the actual arms by an intermediate insulative layer. This also involves very complicated manufacture, and, owing to the small dimensions of such instruments, defective operation cannot be excluded.

The object of the invention is to unite in a generic surgical grasping instrument, in which the two arms are pivotable relative to each other and only a single push-and-pull rod is provided, a mechanically uncomplicated construction, on the one hand, and an electrical insulation of the two arms of the grasping tool, on the other hand.

SUMMARY OF THE INVENTION

This object is accomplished in accordance with the invention in a bipolar surgical grasping instrument of the kind described at the outset by the push-and-pull rod and the toggle lever elements of the two arms consisting of electrically conducting material and being electrically conductively connected to one another, by the first arm being electrically conductively connected to the toggle lever element associated therewith, by the second arm being connected to the toggle lever element associated therewith via an insulating part, by the second arm being electrically conductively connected via its pivot bearing to the tubular shank, and by the first arm being rotatably mounted on the tubular shank and electrically insulated from the second arm and from the tubular shank.

Accordingly, in this construction both arms are pivoted in opposite directions in a manner known per se via toggle lever elements which are jointly driven via a single push-and-pull rod. This push-and-pull rod forms the one electric pole of the high-frequency voltage source, the other pole is formed by the tubular shank itself.

The toggle lever elements of the drive for both arms are jointly connected to the one voltage source. Only one of the two arms is electrically insulated from the toggle lever element by interposition of the insulating part therebetween. This second arm is, in turn, electrically conductively connected to the tubular shank. In order to avoid a short-circuit here it is sufficient for the other arm, i.e., the first arm electrically connected to the push-and-pull rod, to be electrically isolated from the pivot bearing and from the other arm.

Such a construction can be realized with simple means. The mechanical driving movements remain essentially the same as in conventional tubular shank instruments which are not designed as bipolar instruments.

In accordance with a preferred embodiment, it is particularly advantageous for both arms to be rotatably mounted on the tubular shank via a conductive bearing shaft and for the first arm to be electrically insulated from this bearing shaft. This electrically conductive bearing shaft can then make the electrical connection between the second arm and the tubular shank, while the first arm remains electrically isolated from the tubular shank.

An insulating sleeve surrounding the bearing shaft is preferably arranged between the bearing shaft and the first arm in order to achieve this insulation of the first arm from the bearing shaft.

Herein it is particularly advantageous for the insulating sleeve to form part of the insulating part as it is then unnecessary to provide an additional part for insulating the first arm from the bearing shaft and hence from the tubular shank.

The insulating part is preferably made of a ceramic material, but it is also possible to fabricate the insulating part from plastic material.

In a preferred embodiment provision is made for the insulating part to be plate-shaped and to be embedded in a sandwich-like manner in the longitudinal direction in the area of the pivot bearing between the second arm and the associated toggle lever element. Viewed in the direction of the pivot axis, a three-layered construction toggle lever element/insulating part/second arm is thus obtained.

Herein it is advantageous for the insulating part to rest in surface-to-surface contact via end faces against the toggle lever element, on the one hand, and against the second arm, on the other hand. Torques can be transmitted from the toggle lever element to the second arm via these end faces.

It is also expedient for the areas of the second arm, the insulating part and the toggle lever element associated with the second arm, which rest against one another in sandwich configuration, to have openings in alignment with one another for a bearing shaft to pass therethrough. When inserting the bearing shaft, these three parts are then rotationally fixedly connected to one another by the end faces resting with surface-to-surface contact against one another and can transmit torques from the toggle lever element to the second arm without the need for additional fixing means.

When a bearing shaft is conductively connected to the tubular shank, provision may also be made for the insulating part to surround and electrically insulate the adjacent areas of the toggle lever element associated with the second arm from the bearing shaft. There is then no necessity for separate parts for insulating this toggle lever element from the bearing shaft.

It is also particularly advantageous for the first arm and the toggle lever element associated therewith to be of integral construction.

The insulating part can be of such shape that after insertion of the bearing shaft, the second arm, the insulating part and the associated toggle lever element form a rigid component which is of mirror imaged shape in relation to the first arm and the toggle lever element associated therewith. Two arms having dimensions corresponding to those of conventional arms are thus obtained, but with the one arm being interrupted by insertion of the insulating part so as to enable electrical insulation from the bearing shaft, the toggle lever element and the other arm.

In a preferred embodiment, provision may also be made for there to be inserted into the tubular shank an insulating sleeve which insulates the push-and-pull rod from the tubular shank and which receives the end of the push-and-pull rod, the toggle lever elements and the pivot bearing of the first and second arms between legs oriented forwards and parallel to each other. This insulating sleeve additionally centers the push-and-pull rod in the tubular shank and provides electrical insulation also of the toggle lever drive from the tubular shank.

The following description of preferred embodiments of the invention serves in conjunction with the appended drawings to explain the invention in more detail.

DETAILED DESCRIPTION OF THE INVENTION

Figure 1:
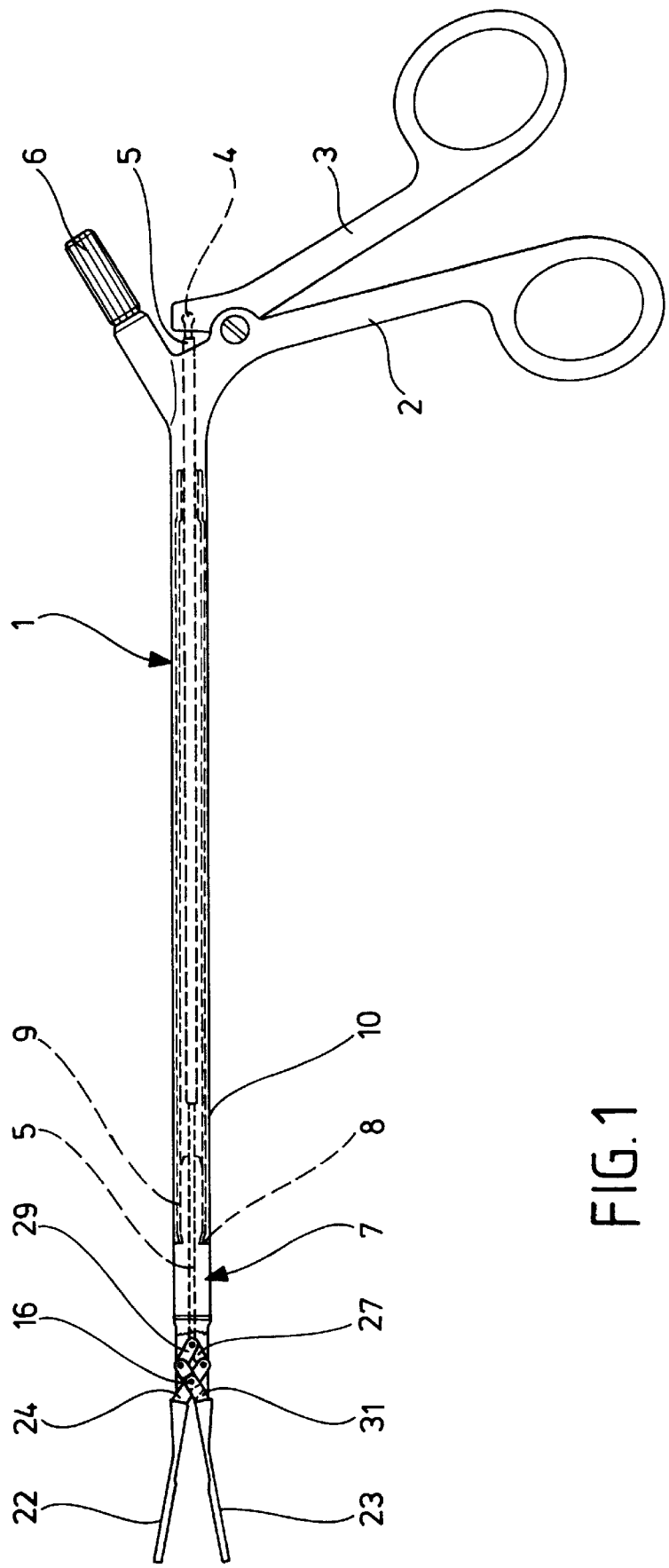
FIG. 1 an overall side view of a bipolar surgical grasping instrument.
Figure 2:
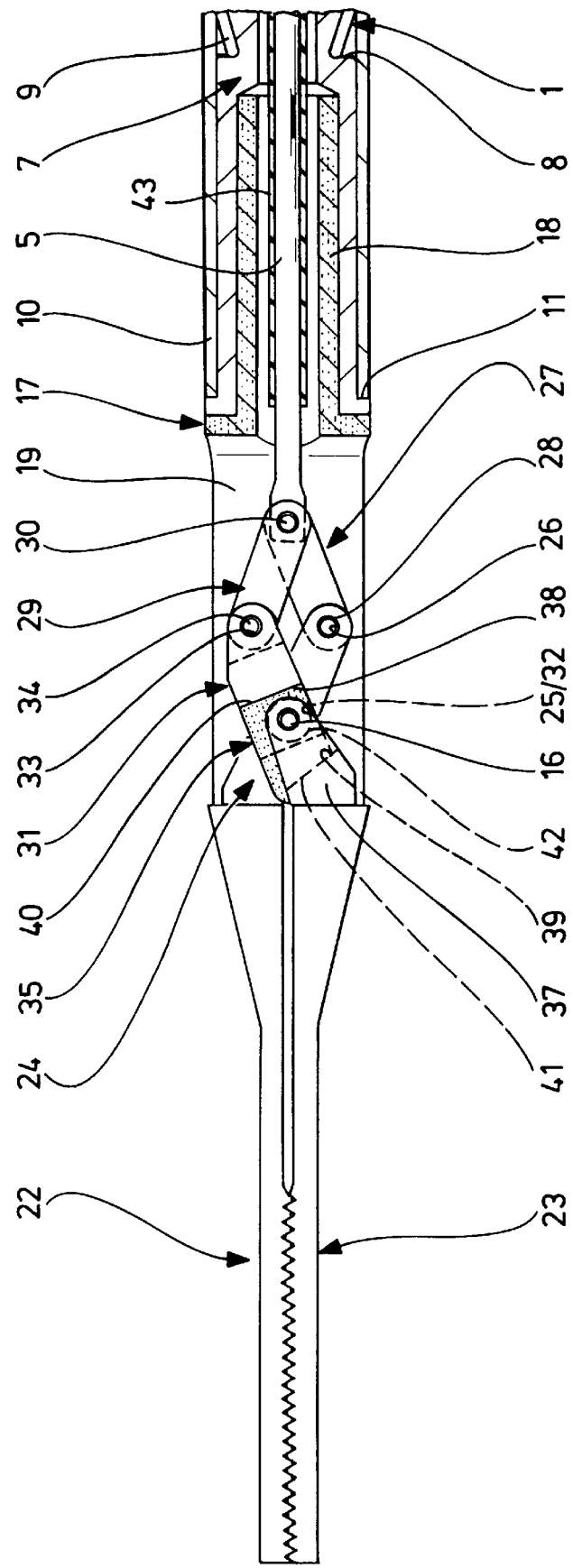
FIG. 2 an enlarged side view of the front area of the instrument of FIG. 1 in a partial, longitudinal, sectional representation.
Figure 3:
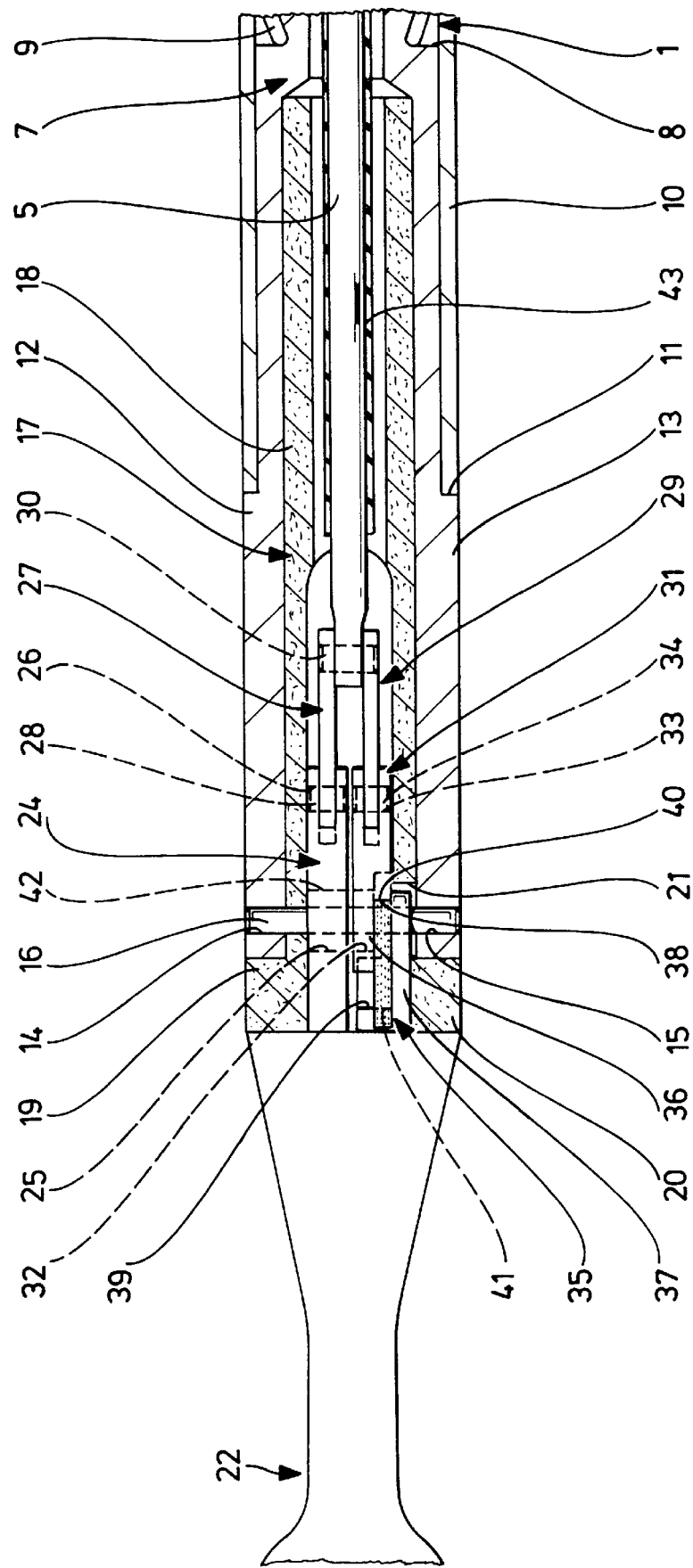
FIG. 3 a view similar to FIG. 2 with the instrument turned through 90° about the longitudinal axis.

The tubular shank instrument illustrated in the drawings comprises an elongate tube 1 which is fixedly connected at its rearward end to a handle member 2. A second handle member 3 which is connected via a spherical head connection 4 to a push-and-pull rod 5 extending in the interior of the tube 1 is mounted on the handle member 2 for pivotal movement about an axis of rotation extending transversely to the longitudinal direction of the tube 1.

The tube 1 is connectable via a plug-in connection 6 to the first pole of a high-frequency voltage source which is not illustrated in the drawings. The push-and-pull rod 5 is similarly connectable via a connection, not recognizable in the drawings, to the other pole of this high-frequency voltage source.

The tube 1 and the push-and-pull rod 5 are electrically insulated from one another. This can be effected in the area of the handle members 2 and 3, for example, by the push-and-pull rod 5 being interrupted in its length by an intermediate insulating part and by the connection of the push-and-pull rod 5 to the voltage source being made in advance of the location of this interruption.

A tube section 7 made of an electrically conducting material, preferably also consisting of metal, is pushed into the front end of the tube 1. This tube section 7 has at its end which is pushed into the tube 1 an annular groove 8 in which wall portions 9 of the tube 1, which are in the form of tongues owing to lengthwise cuts, engage in such a way that the tube section 7 can only be pulled out of the tube 1 when these tongue-shaped wall portions 9 are bent elastically outwards. Such bending of the wall portions 9 can be prevented by a sleeve 10 covering the wall portions 9 in the area of the annular groove 8. The sleeve 10 is mounted for displacement in the longitudinal direction on the tube 1 and normally strikes a step 11 of the tube section 7. However, if this sleeve 10 is pulled back to the extent that wall portions 9 and annular groove 8 are released, the wall portions 9 can be bent elastically outwards and the tube section 7 can then be pulled out of the tube 1.

The tube section 7 carries at its end protruding from the tube 1 two legs 12, 13 oriented forwards and parallel to each other. Arranged at the free ends thereof in alignment with each other are two openings 14, 15 for receiving a bearing shaft 16 made of electrically conducting material and joining the two legs 12, 13.

An insulating member 17 made of an injection molded ceramic material and similar in shape to that of the tube section 7 itself is inserted into the tube section 7. A sleeve-shaped part 18 projects into the closed part of the tube section 7, and two parallel legs 19, 20 integrally connected to the sleeve-shaped part 18 rest against the inside of the legs 12, 13 of the tube section 7. The legs 19 and 20 protrude slightly over the legs 12 and 13. In the area of the openings 14 and 15 in the legs 12 and 13, respectively, the legs 19 and 20 also have recesses 21 through which the bearing shaft 16 can extend.

The push-and-pull rod 5 extends in the interior of the sleeve-shaped part 18 of the insulating member 17 and terminates between the two legs 19 and 20. This push-and-pull rod is centered by the insulating member 17 and electrically insulated from the tube section 7 and hence from the tube 1. In addition, the push-and-pull rod 5 is surrounded by an insulating tube 43.

The bearing shaft 16 forms a pivot bearing for two arms 22 and 23 of a forceps-type or possibly also scissors-type instrument which are mounted by means of the bearing shaft 16 on the tube 1 for pivotal movement in opposite directions. The first arm 22 consists of an electrically conducting material, in particular, metal, and is integrally connected to an extension which forms a toggle lever element 24. This extension contains an opening 25 through which the bearing shaft 16 extends and a further opening 26 through which a bearing pin 28 articulatedly joining the toggle lever element 24 to a further toggle lever element 27 can be inserted. The bearing pin 28 is articulatedly connected at its opposite end to the end of the push-and-pull rod 5.

The toggle lever element 24 and the toggle lever element 27 together form a toggle lever whose angle is adjustable by pushing the push-and-pull rod 5 forwards and backwards as the toggle lever element 24 is mounted stationarily but pivotably relative to the tube 1 in the area of the opening 25. This pivotal movement of the toggle lever element 24 causes pivotal movement of the first arm 22 as the toggle lever element 24 is integrally formed on the first arm 22.

A similar toggle lever is formed by a toggle lever element 29 corresponding to the toggle lever element 27 and articulatedly connected via a bearing pin 30 to the push-and-pull rod 5. The toggle lever element 29 is articulatedly connected to a further toggle lever element 31 via a bearing pin 34. This toggle lever element also corresponds to the toggle lever element 24 of the first arm and like it has an opening 32 for the bearing shaft 16 to extend therethrough and an opening 33 for receiving the bearing pin 34 which articulatedly connects the two toggle lever elements 29 and 31 to each other.

In contrast to the toggle lever element 24, however, this toggle lever element 31 is not integrally connected to the second arm 23, but constitutes a separate component. In this case, a connection between this toggle lever 31 and the second arm 23 is made by an insulating part 35 inserted between the two components. The insulating part 35 preferably consists of injection molded ceramic material, but may also be made of plastic. This insulating part 35 is plate-shaped and lies in the longitudinal direction between similarly plate-shaped lugs 36 and 37 of the toggle lever element 31 and the second arm 23, respectively. This results in a sandwich-like structure, in which in the direction of the bearing shaft 16, the lug 36, the insulating part 35 and the lug 37 rest with surface-to-surface contact against one another.

The lug 36 and the lug 37 each have a step 38 and 39, respectively, against which the rearward end face 40 and the front end face 41 of the plate-shaped insulating part 35 respectively rest in surface-to-surface contact therewith.

A sleeve 42 is formed on one side of the plate-shaped insulating part 35. The sleeve 42 extends through the opening 32 of the toggle lever element 31 and the opening 25 of the toggle lever element 24 and surrounds the bearing shaft 16 which is thereby electrically insulated from the two toggle lever elements 24 and 31.

With the exception of the sleeve 42, the first arm 22 with the toggle lever element 24 formed thereon is of the same design in mirror image as the component comprised of the second arm 23, the insulating part 35 and the toggle lever element 31.

The toggle lever elements 24, 27, 29 and 31 consist of electrically conducting material and are electrically conductively connected to one another and to the push-and-pull rod 5. This results in an electrically conductive connection of the first arm 22 to the push-and-pull rod 5. On the other hand, the second arm 23 is electrically insulated by the insulating part 35 from the toggle lever element 31 and hence also from the push-and-pull rod 5.

The bearing shaft 16 is in electrically conductive connection with the tube section 7 and hence with the tube 1 and, in addition, with the arm 23. It is, however, electrically insulated by the insulating part 35 and, in particular, its sleeve 42, from all of the toggle lever elements 24, 27, 29 and 31, and thus also from the push-and-pull rod 5. An electrical separation of the arms 22 and 23 is thus achieved, in particular, without any structural measures involving high expenditure, merely by inserting the insulating part 35. This construction makes it possible to use such instruments selectively as bipolar instruments or without the application of electrical energy.

If the arm 23 is integrally formed on the toggle lever element 31, in accordance with the design of the arm 22, the electrical insulation is eliminated and this instrument can then be employed in the conventional way. If this one-part arm 23 is replaced by a three-part arm including an inserted insulating part 35, without otherwise altering the construction the two arms can be electrically insulated from one another, the one arm can be electrically connected to the push-and-pull rod 5 and the other arm to the tube section 7 and hence to the tube 1.

Figure 4:
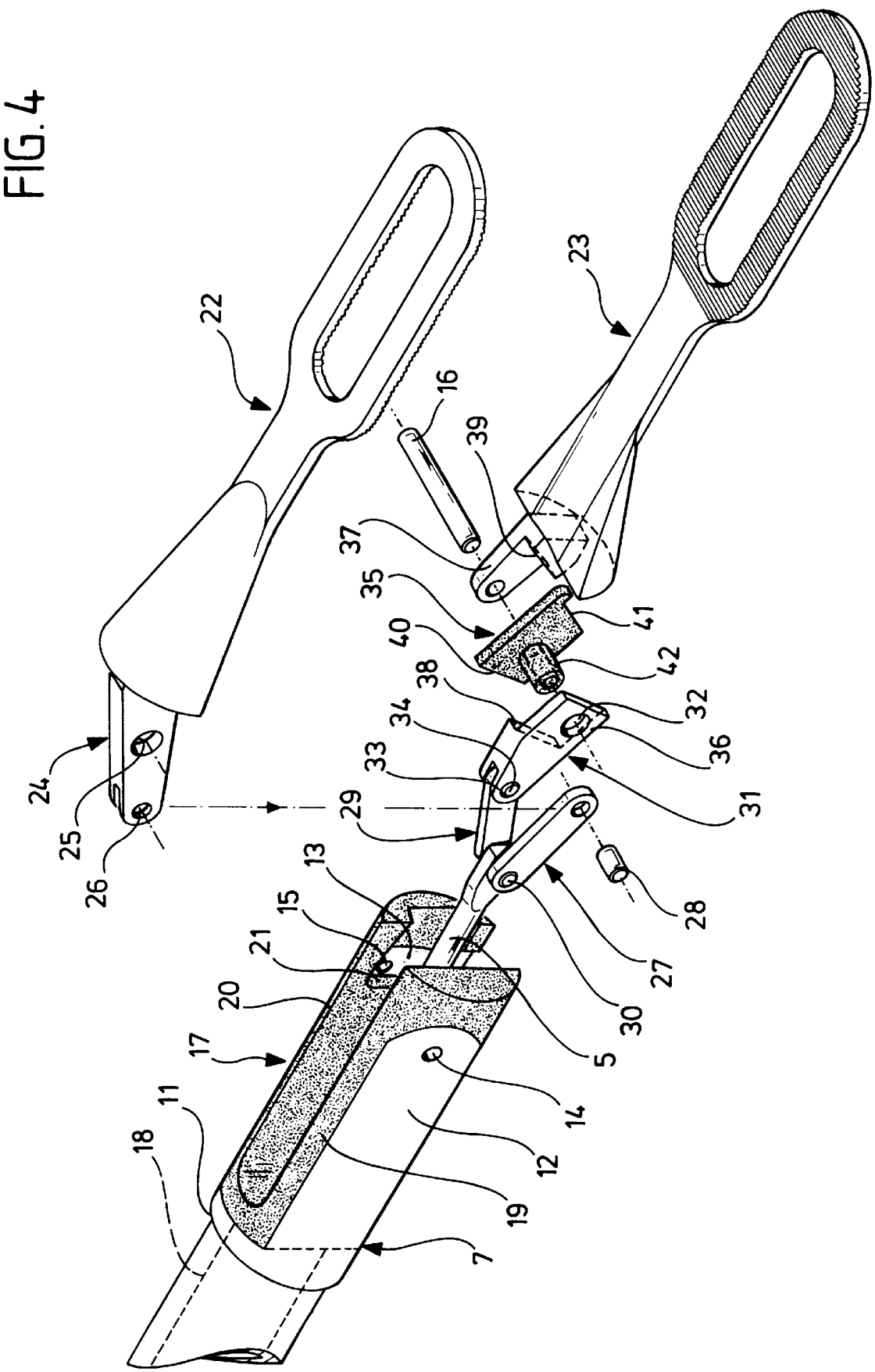
FIG. 4 an exploded view of the front part of the instrument of FIG. 1.

Owing to this particularly simple construction, the instrument can also be disassembled and cleaned in an extremely simple way. This is particularly clear from the illustration in FIG. 4 which shows that by pulling out the bearing shaft 16 and the bearing pin 28 disassembly is possible to a considerable extent once the push-and-pull rod 5 is pulled forwards out of the tube section 7.

What is claimed is:

1. A bipolar surgical grasping instrument, comprising:
a tubular shank;
first and second arms with associated toggle lever elements;
said first and second arms mounted pivotably at an end of said tubular shank;
said first and second arms adapted to be pivoted via said toggle lever elements by a push-and-pull rod that is displaceable in said tubular shank;
said toggle lever elements being electrically conductively connected to one another;
an insulating part for electrically insulating said second arm from said toggle lever elements;
said insulating part transmitting a pivoting force from at least one of said toggle lever elements to said second arm;
a pivot bearing extending through said second arm and at least one of said toggle lever elements;
said first and second arms pivotable about said pivot bearing; wherein:
said second arm is electrically conductively connected with said tubular shank via said pivot bearing; and
said first arm is electrically insulated from said pivot bearing and said second arm.

2. The instrument of claim 1, wherein:
said pivot bearing comprises a conductive bearing shaft; and
said first and second arms are mounted on said tubular shank for rotation with respect to said bearing shaft; and
first arm is electrically insulated from said bearing shaft.

3. The instrument of claim 2, further comprising:
an insulating sleeve surrounding at least part of said bearing shaft, and arranged between said bearing shaft and said first arm.

4. The instrument of claim 3, wherein:
said insulating sleeve forms part of said insulating part.

5. The instrument of claim 2, wherein:
said insulating part comprises ceramic material.

6. The instrument of claim 2, wherein:
said insulating part comprises plastic material.

7. The instrument of claim 2, further comprising:
an insulating sleeve inserted into said tubular shank for electrically insulating said push-and-pull rod from said tubular shank;
said insulating sleeve comprising legs extending parallel to one another toward said first and second arms;
said legs adapted to receive an end of said push-and-pull rod, said toggle lever elements, and said pivot bearing.

8. The instrument of claim 1, wherein:
said insulating part comprises ceramic material.

9. The instrument of claim 1, wherein:
said insulating part comprises plastic material.

10. The instrument of claim 1, wherein:
said insulating part is plate-shaped and is sandwiched between said second arm and the associated toggle lever element of said second arm.

11. The instrument of claim 10, wherein:

said insulating part rests in surface contact via end faces thereof against the associated toggle lever element of said second arm, and against said second arm.

12. The instrument of claim 11, wherein:

said pivot bearing comprises an electrically conductive bearing shaft;

areas of said second arm, said insulating part, and said associated toggle lever element of said second arm, which rest against one another in a sandwiched configuration, have openings in alignment with one another for said bearing shaft passing therethrough.

13. The instrument of claim 12, wherein:

when said bearing shaft is conductively connected to said tubular shank, said insulating part surrounds and electrically insulates adjacent areas of said toggle lever element associated with said second arm from said bearing shaft.

14. The instrument of claim 1, wherein:

said first arm and said toggle lever element associated therewith are of integral construction.

15. The instrument of claim 1, further comprising:

an insulating sleeve inserted into said tubular shank for electrically insulating said push-and-pull rod from said tubular shank;

said insulating sleeve comprising legs extending parallel to one another toward said first and second arms;

said legs adapted to receive an end of said push-and-pull rod, said toggle lever elements, and said pivot bearing.

16. A bipolar surgical grasping instrument, comprising:

a tubular shank;

first and second arms mounted pivotably at an end of said tubular shank;

said first arm extending from an operating end thereof to a first toggle lever element associated therewith;

said first toggle lever element associated with said first arm pivotably mounted about a first pivot point to a second toggle lever element associated with said first arm;

said second toggle lever element associated with said first arm adapted to be pivotably mounted about a second pivot point to a push-and-pull rod that is displaceable in said tubular shank;

said second arm extending from an operating end thereof to a first toggle lever element associated therewith via an insulating part for electrically insulating said second arm from said first toggle lever element associated therewith, and from said first toggle lever element associated with said first arm;

said insulating part transmitting a pivoting force from said first toggle lever element associated with said second arm to said second arm;

said first toggle lever element associated with said second arm pivotably mounted about a third pivot point to a second toggle lever element associated with said second arm;

said second toggle lever element associated with said second arm adapted to be pivotably mounted about said second pivot point; and a bearing shaft extending though said second arm and said first toggle lever element associated with said first arm to allow said second arm to pivot with respect to said first arm; wherein:

said second arm is electrically conductively connected to said tubular shank via said bearing shaft; and said first arm is electrically insulated from said second arm, said bearing shaft, and said tubular shank.

17. The instrument of claim 16, wherein:

said second arm comprises a plate shaped lug through which said bearing shaft extends.

18. The instrument of claim 16, wherein:

said insulating part comprises a plate-shaped portion with a front end face and opposing rear end face;

plate shaped lug of said second arm having a step against which said front end face rests; and said first toggle lever element associated with said second arm comprises a plate shaped lug through which said bearing shaft extends, and which has a step against which said rear end face rests.

19. The instrument of claim 18, wherein:

said step of said first toggle lever element associated with said second arm has a height parallel to a longitudinal axis of said bearing shaft corresponding substantially to a width of said plate-shaped portion of said insulating part.

20. The instrument of claim 18, wherein:

said insulating part comprises a sleeve extending from said plate-shaped portion for surrounding at least part of said bearing shaft, and for extending through an opening in said first toggle lever element associated with said first arm.

* * * * *